United States Patent [19]

Dieterich

[11] 4,147,653

[45] Apr. 3, 1979

[54] STORABLE MIXTURES CONTAINING AROMATIC ISOCYANATOSULPHONIC ACIDS

[75] Inventor: Dieter Dieterich, Leverkusen, Fed. Rep. of Germany

[73] Assignee: Bayer Aktiengesellschaft, Leverkusen, Fed. Rep. of Germany

[21] Appl. No.: 842,428

[22] Filed: Oct. 14, 1977

[30] Foreign Application Priority Data

Oct. 30, 1976 [DE] Fed. Rep. of Germany ....... 2650172

[51] Int. Cl.$^2$ .................. C07C 119/042; C08G 18/79
[52] U.S. Cl. .............................. 252/182; 260/453 SP
[58] Field of Search .............. 260/453 SP; 106/287 R, 106/287; 252/182

[56] References Cited

U.S. PATENT DOCUMENTS 3,449,256  6/1969  Farrissey et al. .............. 260/453 SP
3,826,769  7/1974  Carlson .......................... 260/75 NT Primary Examiner—Theodore Morris
Attorney, Agent, or Firm—Gene Harsh; Joseph C. Gil

[57] ABSTRACT

The instant invention is directed to storage stable mixtures in the form of solutions or solution-suspensions comprising:
  (a) from 10 to 80 percent by weight of aromatic isocyanatosulphonic acids;
  (b) from 20 to 90 percent by weight of a liquid ester of an inorganic or organic acid of phosphorous, which liquid ester represents a solvent for the aromatic isocyanato sulphonic acids; and
  (c) from 0 to 70 percent by weight of non-sulphonated organic polyisocyanates;

said percents by weight based on the total weight of (a)+(b)+(c).

The mixtures of the instant invention are useful in producing isocyanate addition products.

4 Claims, No Drawings

STORABLE MIXTURES CONTAINING AROMATIC ISOCYANATOSULPHONIC ACIDS

BACKGROUND OF THE INVENTION

Sulphonic acids of aromatic diisocyanates and polyisocyanates are known. They are readily obtained by reacting the corresponding aromatic diisocyanates or polyisocyanates with sulphonating agents, such as sulphur trioxide, adducts of sulphur trioxide, oleum, chlorosulphonic acid or sulphuric acid (see, for example German Offenlegungsschriften Nos. 2,227,111 and 2,357,615, and U.S. Pat. No. 3,826,769). It is possible to obtain solid, resin-like or powder-form sulphonation products or solutions of the sulphonated isocyanates in unreacted starting isocyanate, depending upon the isocyanate used and upon the degree of sulphonation.

Although no difficulties are involved in handling liquid sulphonated polyisocyanates, considerable problems arise in the production, storage and use of solid powder-form isocyanatosulphonic acids. These products are obtained in such finely divided form during their production that they are difficult to separate from the liquid reaction medium and to purify. The dried products give off dust during packaging and re-packaging. More importantly, however, dry powders produced in this way are not stable in storage. During storage, the melting or decomposition point increases and the products become increasingly insoluble in organic solvents and in the polyesters, polyethers and polyols normally used in the production of polyurethanes.

Although the problem of adequate stability in storage is generally prevalent in the case of polyisocyanates and is therefore known in principle to those skilled in the art, the deterioration in quality, after production in the case of solid powder-form isocyanatosulphonic acids occurs so quickly (for example after only a few days) that the production of technically useful polyaddition products is made extremely difficult, if not impossible.

On the other hand, there is a commercial need to use polyisocyanatosulphonic acids in addition to or instead of the conventional diisocyanates and polyisocyanates in polyaddition chemistry because these isocyanates are excellent starting products for the production of hydrophilic, especially water-dispersible polyurethanes. In addition, they appear particularly favorable from the physiological and industrial hygiene point of view because they have substantially no vapor pressure and, upon degradation, form water-soluble aminosulphonic acids.

Hitherto, polyurethanes based on sulphonated tolylene diisocyanate have been produced either by sulphonating the prepolymer produced from the pure diisocyanate rather than the diisocyanate itself (U.S. Pat. No. 3,826,769) or by producing the isocyanatosulphonic acid only shortly before further processing into the polyurethane (U.S. Pat. No. 3,826,769). The disadvantage of the first method is that there are limitations on the use of the sulphonating agent because sulphur trioxide, for example, can decompose the polyether prepolymers. If sulphuric acid is used for sulphonation, simultaneous chain-extension to form urea groups is unavoidable. In addition, it is only possible by this method to sulphonate completely or partly free isocyanates, but not products in the form of urethanes. In the case of an NCO-prepolymer, therefore, it is only the terminal isocyanate units which are sulphonated. The second method is generally not performed on a commercial scale because the manufacturer of a polyurethane cannot be expected to carry out an isocyanate sulphonation process beforehand.

It has also been proposed (U.S. Pat. No. 3,826,769) to dissolve the isocyanatosulphonic acids immediately after the production thereof in an organic solvent, for example acetone, and to use them in the form of a solution. This method is also unsuitable for operation on a commercial scale because, for example, a solution of sulphonated tolylene diisocyanate in acetone is only stable for at most a few hours, after which clouding and sedimentation quickly occur.

Accordingly, it is not surprising that solid isocyanatosulphonic acids have hitherto not been adopted for use on a commercial scale.

Accordingly, there was a need to produce and stabilize isocyanatosulphonic acids in such a way that they may be readily stored and used, retaining their solubility in organic media even after prolonged storage.

In addition, there is a commercial need for a solvent for aromatic isocyanatosulphonic acids which is capable of taking up as large as possible a quantity of the isocyanatosulphonic acids and enables these substances to be further reacted in homogeneous phase.

DESCRIPTION OF THE INVENTION

The present invention provides a way of satisfying these various needs. It has surprisingly been found that liquid esters of inorganic or organic acids of phosphorus, providing they do not contain any long-chain apolar hydrocarbon residues in their molecule, are good solvents for aromatic isocyanatosulphonic acids which are known to be difficult to dissolve and to melt at high temperatures. In addition, saturated solutions of the aromatic isocyanatosulphonic acids in these solvents are excellent suspending agents for the aromatic isocyanatosulphonic acids so that it is possible to obtain mixtures having high concentrations of aromatic isocyanatosulphonic acids in the above-mentioned solvents, an equilibrium existing between the suspended phase and the solution phase, so that such suspension of aromatic isocyanatosulphonic acids in saturated solutions of the aromatic isocyanatosulphonic acids (hereinafter referred to as "solution suspensions") behave like highly concentrated solutions during chemical reactions of the dissolved and suspended aromatic isocyanatosulphonic acids. In addition, the solvent in such systems increases the stability in storage of the dissolved and, optionally, additionally suspended aromatic isocyanatosulphonic acids.

Accordingly, the present invention relates to storage stable mixtures in the form of a solution or solution-suspension containing, based on the total quantity of (a)+(b)+(c):

(a) from 10 to 80%, by weight, of aromatic isocyanatosulphonic acids;

(b) from 20 to 90%, by weight of a liquid ester of an inorganic or organic acid of phosphorus which represents a solvent for the aromatic isocyanatosulphonic acids;

(c) from 0 to 70%, by weight, of non-sulphonated organic polyisocyanates;

and, optionally, other auxiliaries and additives.

The esters of the inorganic or organic acids of phosphorus present in the mixtures according to the present invention are also good solvents and complex-formers for the sulphonating agents used for sulphonation, and especially for sulphur trioxide. Some of the above-mentioned esters, which are otherwise inert with respect to the sulphonating agents used, may therefore be used with advantage for producing the mixtures according to the present invention during the actual sulphonation of the aromatic isocyanates, so that the mixtures according to the present invention are directly formed during this sulphonation process.

Accordingly, the present invention also relates to a process for producing the mixtures according to the present invention, wherein aromatic isocyanates are sulphonated in the presence of liquid esters of inorganic or organic acids of phosphorus which are inert with respect to sulphonating agents and which represent a solvent for aromatic isocyanato-sulphonic acids.

It is, of course, also possible to mix the isocyanatosulphonic acids produced by known methods with the above-mentioned esters in a separate operation.

The mixtures according to the present invention may be produced using any solid aromatic isocyanatosulphonic acids of the type obtained in finely divided form during the sulphonation of mono-, di- or poly-isocyanates. Examples include the sulphonation products of: phenyl isocyanate; p-tolyl isocyanate; p-chlorophenyl isocyanate; p-nitrophenyl isocyanate; p-methoxyphenyl isocyanate; m-chlorophenyl isocyanate; m-chloromethyl phenyl isocyanate; p-chloromethyl phenyl isocyanate; 4,4'-stilbene diisocyanate; 4,4'-dibenzyl diisocyanate; 3,3'- and 2,2'-dimethyl-4,4'-diisocyanatodiphenyl methane; 2,5,2',5'-tetramethyl-4,4'-diisocyanatodiphenyl methane; 3,3'-dimethoxy-4,4'-diisocyanatodiphenyl methane; 3,3'-dichloro-4,4'-diisocyanatodiphenyl methane; 4,4'-diisocyanatodimethyl methane; 4,4'-diisocyanatodiphenyl cyclohexyl methane; 4,4'-diisocyanatobenzophenone; 4,4'-diisocyanatodiphenyl sulphone; 4,4'-diisocyanatodiphenyl ether; 4,4'-diisocyanato-3,3'-dibromidiphenyl methane; 4,4'-diisocyanato-3,3'-diethyl diphenyl methane; 4,4'-diisocyanatodiphenyl-1,2-ethylene; 4,4'-diisocyanatodiphenyl sulphide; 1,3- and 1,4-phenylene diisocyanate; 2,4- and 2,6-tolylene diisocyanate and mixtures of the isomers; diphenyl methane-2,4'- and/or -4,4'-diisocyanate; naphthylene-1,5-diisocyanate; triphenyl methane-4,4',4''-triisocyanate; polyphenyl polymethylene polyisocyanates of the type obtained by condensing aniline with formaldehyde, followed by phosgenation, and described, for example, in British Pat. Nos. 874,430 and 848,671; polyisocyanates containing carbodiimide groups of the type described in German Pat. No. 1,092,007; diisocyanates of the type described in U.S. Pat. No. 3,492,330; polyisocyanates containing allophanate groups of the type described, for example, in British Pat. No. 994,890, Belgian Pat. No. 761,626 and published Dutch patent application No. 7,102,524; polyisocyanates containing isocyanurate groups of the type described, for example, in German Pat. Nos. 1,022,789; 1,222,067 and 1,027,394, and in German Offenlegungsschriften Nos. 1,929,034 and 2,004,048; polyisocyanates containing acylated urea groups as described in German Pat. No. 1,230,778; polyisocyanates containing biuret groups of the type described, for example, in German Pat. No. 1,101,394, in British Pat. No. 889,050 and in French Pat. No. 7,017,514; and the like.

It is preferred to use powder-form sulphonated diisocyanates and triisocyanates, especially the monosulphonic acids and disulphonic acids, generally in the form of the dimers, of 4,4'-diisocyanatodiphenyl methane, 2,4'-diisocyanatodiphenyl methane and, in particular, 2,4-diisocyanatotoluene and 2,6-diisocyanatotoluene and the mixtures of these isomers. The production of such powder-form polyisocyanates is known and is described, for example, in U.S. Pat. No. 3,826,769, in German Offenlegungsschrift No. 25 24 476 which corresponds to U.S. patent application Ser. No. 690,494 filed on May 27, 1976 or in German Offenlegungsschrift No. 26 15 876 which corresponds to U.S. patent application Ser. No. 782,642 filed on Mar. 30, 1977.

As is known, powder-form aromatic isocyanatosulphonic acids to be stabilized in accordance with the present invention are generally formed by carrying out sulphonation in excess isocyanate or in an inert organic suspending agent, such as dichloroethane or tetrachloroethane. In addition, the particle size of the isocyanatosulphonic acids obtained in the form of finely divided powders may be adjusted by suitably selecting the suspending agent, the temperature at which sulphonation is carried out and the stirring speed during sulphonation. The addition of surfactants generally leads to a reduction in the particle size. The aromatic isocyanatosulphonic acids to be stabilized in accordance with the present invention will generally have an average particle diameter of from 0.005 to 0.5 mm.

Suitable solvents for the aromatic isocyanatosulphonic acids are any esters, liquid at room temperature, of inorganic or organic acids of phosphorus providing they do not contain any aliphatic hydrocarbon residues having more than 7 carbon atoms in the chain. Suitable esters of this type include those of phosphoric acid, pyrophosphoric acid, phosphorous acid and the optionally halogen-substituted benzene and $C_1$–$C_6$ alkane phosphonic acids. In the case of phosphoric acid and phosphorous acids, both the diesters and the triesters may be used. In the case of pyrophosphoric acid, the tetraesters are particularly suitable while, in the case of phosphonic acids, the diesters are particularly suitable. It is preferred to use the esters of the above-mentioned acids, complying with the above requirements, with optionally chlorine- or bromine-substituted monohydric phenols or cresols or monohydric $C_1$–$C_7$, preferably $C_1$–$C_3$, alkanols. Chlorine- or bromine-substituted triaryl phosphates or tris-($C_1$–$C_3$ alkyl)-phosphates are particularly preferred solvents for the mixtures according to the present invention.

Esters which may actually be used as reaction medium for the sulphonation of the aromatic isocyanates include those of the above-mentioned type which, in addition to their complex-forming capacity with the sulphonating agents, especially sulphur trioxide, are inert with respect to the sulphonating agents, i.e., cannot themselves be sulphonated under the sulphonation conditions. Such esters include the above-mentioned esters containing only alkyl radicals which may optionally be chlorine- or bromine-substituted. Most preferred are the chlorine- or bromine-substituted-($C_1$–$C_3$ alkyl)-phosphates.

Examples of suitable solvents and, in the absence of sulphonatable aromatic residues, esters which may be simultaneously used as reaction medium for the sulphonation reaction are: trimethyl phosphate, triethyl phosphate, tripropyl phosphate, tributyl phosphate, trihexyl phosphate, triphenyl phosphate, tricresyl phosphate, also mixed phosphates, such as diethyl propyl phosphate, diphenyl cresyl phosphate, trimethyl phosphite, triethyl phosphite, tripropyl phosphite, diethyl phosphate, dipropyl phosphate, bis-chloroethyl phosphate, bis-bromoethyl phosphate, bis-dibromopropyl phosphate, dipropyl phosphite, triethyl phosphite, chloromethane phosphonic acid-bis-(2-chloroethyl)-ester, methane phosphonic acid dibutyl ester, chloromethanephosphonic acid-bis-(4-chlorophenyl)-ester, benzene phosphonic acid-bis-(2-chloroethyl)-ester or pyrophosphoric acid tetraethyl ester. Cyclic phosphates and phosphites, such as 2-ethoxy-1,3,2-dioxaphospholane, 2-ethoxy-1,3,2-dioxaphosphorinane or 2-oxo-2-methyl-1,3-dioxa-2-phosphacycloheptane are also suitable, although less preferred.

Liquid mixtures of these esters, which may also contain a component which is solid in pure form, are also suitable.

It is particularly preferred to use tris-chloroethyl phosphate, tris-bromoethyl phosphate, dichloroethyl bromoethyl phosphate, tris-dibromopropyl phosphate, tris-dichloropropyl phosphate and halogenated triaryl phosphates.

The procedure preferably adopted in accordance with the present invention for producing the new liquid mixtures containing isocyanatosulphonic acids comprises carrying out sulphonation of the isocyanates in the presence of the above-mentioned phosphates, phosphites or phosphonates at temperatures of from 0° to 140° C.

For example, for sulphonating tolylene diisocyanate, it is possible instead of using pure sulphur trioxide or oleum to use a solution of these sulphonating agents in tris-chloroethyl phosphate. To this end, 1 mol of sulphur trioxide or a corresponding quantity of oleum is dissolved in from 1 to 4 mols of the phosphate. It is also possible to use a smaller quantity of the phosphate, for example 0.5 mol, when the solution or complex is prepared in situ by simultaneously adding oleum or sulphur trioxide and phosphate through a common inlet pipe. The presence of the phosphate deactivates and dilutes the sulphonating agent so that sulphonation takes place less virogously and more uniformly. In this way, undesirable coarse deposit or lump formation is generally avoided in and around the inlet. The sulphonating agent may be added much more quickly than is the case where sulphur trioxide or oleum is used. Solutions or "solution-suspensions" of the isocyanatosulphonic acids are obtained, depending upon the quantitative ratio in which the isocyanate, sulphonating agent and phosphate (or phosphite or phosphonate) are used. It is possible to produce, for example, from about 20 to 30% solutions of sulphonated tolylene diisocyanate in trischloroethyl phosphate. Larger quantities of the sulphonated isocyanate are suspended in finely divided form by the viscous solution. The suspended fractions pass into solution at a rate commensurate with that at which the dissolved fraction reacts off in a secondary reaction, for example by reaction with polyols. It is also possible initially to mix the phosphate, phosphite or phosphonate with the isocyanate and then to carry out sulphonation in the conventional way.

The above reaction may, of course, also be carried out in the presence of inert solvents, such as dichloroethane or chlorobenzene. In this case, the solvent is, in general, completely or partly removed by distillation on completion of the reaction. In another embodiment of the process, the sulphonated isocyanate is produced in known manner in the absence of phosphates, phosphites or phosphonates and in the presence or absence of solvent, after which the phosphate, phosphite or phosphonate is added in order to dissolve at least part of the isocyanatosulphonic acid. If this process is carried out in the presence of inert solvents, the isocyanatosulphonic acid is best separated off at the end of the reaction by decantation, filtration or centrifuging and either the still moist or the dried product is mixed with the phosphate, phosphite or phosphonate.

The quantitative ratios between the components present in the mixtures according to the present invention and the quantitative ratios between the starting materials used for the production thereof by direct sulphonation are generally selected in such a way that the mixtures according to the present invention contain (a) from 10 to 80%, by weight, peferably from 20 to 60%, by weight, of aromatic isocyanatosulphonic acids; (b) from 20 to 90%, by weight, preferably from 40 to 80%, by weight, of the exemplified esters, and (c) from 0 to 70%, by weight, preferably from 5 to 40%, by weight, of non-sulphonated organic polyisocyanates. All the percentages quoted in this respect are based on the total quantity of (a)+(b)+(c).

In addition, the mixtures according to the present invention may contain additives in small quantities to increase the stabilizing effect or to obtain additional stabilizing effects, for example against yellowing. Such additives include light stabilizers known to those skilled in the art, such as sterically hindered phenols, UV-absorbers, also organopolysiloxanes and chlorofluorocarbon oils. The stabilized preparations are storable and transportable and are suitable for the production of a variety of different types of polyurethanes, for example elastomers, foams, coatings, shaped articles and adhesives.

The polyisocyanates mentioned under (c) are not only the above-mentioned aromatic polyisocyanates, but also polyisocyanates containing aliphatically or cycloaliphatically bound isocyanate groups, such as hexamethylene diisocyanate, 3,3,5-trimethyl-5-isocyanatomethyl cyclohexyl isocyanate or tris-(isocyanatohexyl)-biuret.

The stabilized isocyanatosulphonic acids are soluble in polyesters and polyethers, even after prolonged storage. The polyurethanes produced from them are substantially free from inhomogeneities and clouding. Although it is not possible to prevent transesterification reactions from occurring in the mixtures according to the present invention, such reactions do not adversely affect either the solubility or the reactivity of the isocyanatosulphonic acids. Partial and even extensive esterification, for example in an excess of triethyl phosphate, may even be desirable because it reduces the considerable hydrophilicity of the products.

The liquid mixtures according to the present invention may be widely used as reaction components or even as additives during the production of a variety of different types of polyurethane plastics. They are particularly suitable for use as flameproofing agents and antistatic agents and also as cross-linkers and adhesion promoters for polar, especially mineral substrates.

EXAMPLES

EXAMPLE 1

43.5 g of tolylene diisocyanate (80:20 mixture of 2,4- and 2,6-isomers) are added dropwise over a period of 20 minutes to a solution of 23 g of sulphur trioxide in 87 g of tris-chloroethyl phosphate. The temperature rises to 37° C. and a clear solution is initially formed. After 24 hours, a milky, thinly liquid paste has formed. The product has an isocyanatosulphonic acid content of 42%.

EXAMPLE 2

A solution of 87 g (0.5 mol) of tolylene diisocyanate (80:20 mixture of 2,4- and 2,6-isomers) in 87 g of tris-chloroethyl phosphate is reacted for 4 hours with 43 g of sulphur trioxide, resulting in the formation of a thickly liquid 60% paste of the dimeric tolylene diisocyanate monosulphonic acid in tris-chloroethyl phosphate.

EXAMPLE 3

43.5 g of tolylene diisocyanate (80:20 mixture of 2,4- and 2,6-isomers) are added dropwise over a period of 10 minutes to a solution of 20 g of sulphur trioxide in 174 g of tris-chloroethyl phosphate. A clear 26.7% solution of the dimeric tolylene diisocyanate monosulphonic acid is formed.

EXAMPLE 4

Diisocyanatodiphenyl methane is distilled off from crude phosgenation product of an aniline/formaldehyde condensate until the distillation residue has a viscosity of 400 cP at 25° C. (2-nuclear content: 45%, by weight; 3-nuclear content: 22%, by weight, content of higher nuclear polyisocyanates: 33%, by weight). A solution of 90 g of 65% oleum in 1000 g of tris-chloroethyl phosphate is added with stirring over a period of 10 minutes at room temperature to 560 g of this polyisocyanate mixture. The temperature rises to approximately 35° C. with moderate evolution of $CO_2$. A clear thickly liquid solution of the sulphonated isocyanate is obtained. Despite the very rapid addition of the sulphonating agent, no deposit is formed.

EXAMPLE 5

A solution of 8 g of sulphur trioxide in 50 g of tris-chloroethyl phosphate is added over a period of 5 minutes at room temperature to 56 g of the polyisocyanate characterized in more detail in Example 4 having a viscosity of 400 cP. A clear thickly liquid solution of the sulphonated isocyanate is obtained. Composition of the solution:
36 g of sulphonated polyisocyanate (31%)
28 g of non-sulphonated starting isocyanate (25%)
50 g of tris-chloroethyl phosphate (44%).

EXAMPLE 6

A solution of 6.3 g of 65% oleum in 50 g of tris-chloroethyl phosphate is added over a period of 12 minutes at 28° C. to a solution of 25 g of 4,4'-diisocyanatodiphenyl methane in 50 g of tris-chloroethyl phosphate. An almost clear thinly liquid yellow solution is formed with evolution of $CO_2$.

Comparison Tests

If the tris-chloroethyl phosphate used in Example 6 is replaced by a conventional solvent, for example dichloroethane, tetrachloroethane, chlorobenzene, the sulphonated isocyanate is obtained in the form of a substantially insoluble deposit.

EXAMPLE 7

A solution of 11 g of 65% oleum in 20 g of tris-chloroethyl phosphate is added dropwise over a period of 1 hour at room temperature to a mixture of 60 g of the adduct of 1 mol of tripropylene glycol with 5 mols of 4,4'-diisocyanatodiphenyl methane. The viscosity increases considerably with evolution of $CO_2$. A viscous orange-red solution is obtained after dilution with 60 g of tris-chloroethyl phosphate.

EXAMPLE 8

60 g of tris-chloroethyl phosphate and 40.5 g 65% oleum are added in thin streams to 87 g of tolylene diisocyanate (80:20 mixture of 2,4- and 2,6-isomers) in such a way that both streams are combined and the mixture flows through an approximately 4 cm long inlet tube into the reaction vessel filled with the diisocyanate. A clear viscous solution is initially obtained after an increase in temperature and vigorous foaming, changing into an opaque, white thick paste towards the end of sulphonation. This paste is diluted with 50 g of tris-chloroethyl phosphate and stirred for a further period, during which its viscosity undergoes a considerable increase. A very thickly liquid opaque paste is obtained.

EXAMPLE 9

25 g of 4,4'-diisocyanatodiphenyl methane and 10 g of triethyl phosphate are heated to 40° C., resulting in the formation of a clear solution. A solution of 7.2 g of 65% oleum in 20 g of triethyl phosphate is then stirred in over a period of 5 minutes. Sulphonation takes place with evolution of gas. A thinly liquid solution is obtained.

EXAMPLE 10

250 g of 4,4'-diisocyanatodiphenyl methane and 50 g of triethyl phosphate are heated to 40° C., resulting in the formation of a clear solution. 72 g of 65% oleum and 100 g of triethyl phosphate are then added in thin streams in such a way that both streams are combined and the mixture flows through an approximately 4 cm long inlet tube into the reaction vessel filled with the diisocyanate. A clear viscous solution of the sulphonated isocyanate in triethyl phosphate is obtained with evolution of $CO_2$.

EXAMPLE 11

34.8 g of 2,4-diisocyanatotoluene are added to 70 g of a liquid phenyl-isopropyl phenyl-phosphate mixture (the ortho phosphoric acid triester having been made using 65% by weight of phenol, 18% by weight of 2-isopropyl phenol, 2% by weight of 3-isopropyl phenol and 15% by weight of 4-isopropyl phenol as hydroxyl components). 18 g of 65% oleum are very slowly added dropwise to the mixture. A highly viscous, clouded solution of the sulphonated isocyanate is obtained.

EXAMPLE 12

The procedure is as in Example 10, except that 35 g of 2,4-diisocyanato-toluene are initially introduced, followed by the addition of 18 g of oleum and 70 g of the phenyl isopropyl phenyl phosphate described in more detail in Example 11. An almost clear solution of the sulphonated isocyanate is obtained.

EXAMPLE 13

A mixture of 174 g of 2,4-diisocyanatotoluene and 100 g of triethyl phosphate is sulphonated by the dropwise addition at room temperature of 72 g of 65% oleum. A thinly liquid paste of the sulphonation product in triethyl phosphate is obtained.

EXAMPLE 14

The procedure is as in Example 10, except that 174 g of 2,4-diisocyanatotoluene are initially introduced, followed by the addition of 72 g of oleum and 200 g of triethyl phosphate. A thinly liquid clear solution of the sulphonation product is obtained.

The clear solutions of the sulphonated isocyanates obtained in accordance with Examples 3 to 7, 9, 10, 12 and 14 may be reacted in known manner with hydroxy- and amino-functional compounds to form urethanes and ureas. If the reactants are polyfunctional, polymeric substantially non-inflammable products are obtained in which the phosphate acts as plasticizer and additional flameproofing agent.

EXAMPLE 15

1 part of the phosphate solution of Example 6 is stirred with 1 part of a linear polypropylene glycol ether having a molecular weight of 2000. A cross-linked substantially non-inflammable elastomer is formed after only 2 minutes.

EXAMPLE 16

The dispersions obtained in accordance with Example 2 and Example 8 are soluble after 4 minutes at 60° C. in an excess of polypropylene glycol having a molecular weight of 2000, an oligourethane containing terminal OH-groups being formed.

EXAMPLE 17

10 g of dimeric 2,4-diisocyanatotoluene-5-sulphonic acid are dissolved in 20 g of triethyl phosphite immediately after production in chlorobenzene. A clear storable solution is obtained.

The polyisocyanatosulphonic acids in the form of these solutions are storable and transportable and, even after prolonged storage, may be reacted with conventional isocyanate and/or sulphonic acid reactants.

EXAMPLE 18

Diisocyanatodiphenyl methane is distilled off from crude phosgenation product of an aniline/formaldehyde condensate until the distillation residue has a viscosity of 100 cP at 25° C. (2-nuclear content: 60%, by weight; 3-nuclear content: 21%, by weight; content of higher nuclear polyisocyanates: 19%, by weight). 20 g of 65% oleum are added dropwise with vigorous stirring over a period of 1 hour to 130 g of this polyisocyanate mixture in 100 g of tris-chloroethyl phosphate. 60 g of triethyl phosphate are then added. A thickly liquid homogeneous solution of the sulphonated polyisocyante is obtained. In the absence of the phosphates, a heterogeneous reaction mixture is obtained.

EXAMPLE 19

A mixture is produced from 100 g of the phosgenation product mentioned as starting material in Example 18, 50 g of the solution of the sulphonated polyisocyanate in a phosphate mixture obtained in accordance with Example 18 and 25 g of trichlorofluoromethane. A mixture of 150 g of 44% soda waterglass ($Na_2O$:$SiO_2$ = 1:2), 0.2 g of the sodium salt of a sulphonated paraffin mixture $C_{10}$–$C_{14}$ as emulsifier and 1.5 g of triethylamine is then added all at once. The mixture foams to give a foam having a unit weight of 450 which cannot be ignited in the flame of a Bunsen burner and shows high compressive strength.

What is claimed is:

1. A storable mixture in the form of a solution or solution-suspension comprising, based on the total quantity of (a)+(b)+(c):
   (a) from 10 to 80 percent by weight of aromatic isocyanatosulphonic acids;
   (b) from 20 to 90 percent by weight of a liquid ester of an inorganic or organic acid of phosphorus, which ester represents a solvent for the aromatic isocyanatosulphonic acids;
   (c) from 0 to 70 percent by weight of non-sulphonated organic polyisocyanates.

2. The mixture of claim 1 where Component (a) comprises from 20 to 60 percent by weight, Component (b) comprises 40 to 80 percent by weight and Component (c) comprises from 5 to 40 percent by weight.

3. A process for producing a storable mixture in the form of a solution or solution-suspension comprising, based on the total quantity of (a)+(b)+(c):
   (a) from 10 to 80 percent by weight of aromatic isocyanatosulphonic acids;
   (b) from 20 to 90 percent by weight of a liquid ester of an inorganic or organic acid of phosphorus, which ester represents a solvent for the aromatic isocyanatosulphonic acids;
   (c) from 0 to 70 percent by weight of non-sulphonated organic polyisocyanates said method comprising sulphonating aromatic isocyanates in the presence of liquid esters of inorganic or organic acids of phosphorus which are inert with respect to sulphonating agents and which represent a solvent for aromatic isocyanatosulphonic acids.

4. The process of claim 3 wherein said isocyanates are sulphonated at a temperature of from 0° to 140° C.

* * * * *